United States Patent

Takahashi et al.

[11] 3,945,888
[45] Mar. 23, 1976

[54] METHOD FOR THE PRODUCTION OF CEPHALOSPORINS

[75] Inventors: Takeshi Takahashi; Kenji Kawahara; Toshiyuki Takahashi; Koichi Kato; Yoshio Yamazaki, all of Osaka, Japan

[73] Assignee: Takeda Chemical Industries, Ltd., Japan

[22] Filed: Dec. 4, 1973

[21] Appl. No.: 421,636

[30] Foreign Application Priority Data
Dec. 6, 1972    Japan............................ 47-122205

[52] U.S. Cl..................................... 195/29; 195/30
[51] Int. Cl.²......................................... C12D 9/00
[58] Field of Search...................... 195/29, 36 R, 30

[56] References Cited
UNITED STATES PATENTS
3,816,253   6/1974   Takahashi et al..................... 195/29
3,862,004   1/1975   Takahashi et al..................... 195/29

*Primary Examiner*—Alvin E. Tanenholtz
*Attorney, Agent, or Firm*—Wenderoth, Lind & Ponack

[57] ABSTRACT

A new method for production of a cephalosporin ester (I) which comprises reacting a derivative of an organic acid (II) with a 7-aminocephem compound (III) in the presence of an enzyme of a microorganism of one of the genera Escherichia, Bacillus, Proteus and Pseudomonas:

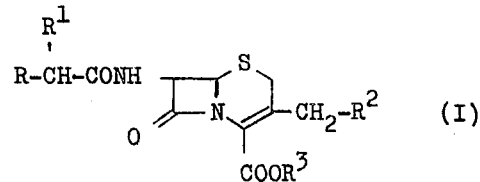

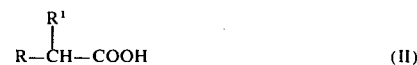

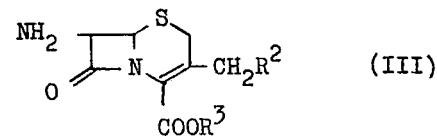

wherein R is an unsaturated six-membered carbocyclic ring or five-membered heterocyclic ring residue which may optionally have uncharged substituent groups; $R^1$ is hydrogen or an uncharged substituent group such as hydroxyl or halogen; $R^2$ is a hydrogen atom or an organic group which is bound through an oxygen, sulfur or nitrogen atom; $COOR^3$ is a group which may easily be converted to COOH.

7 Claims, No Drawings

METHOD FOR THE PRODUCTION OF CEPHALOSPORINS

This invention relates to a new method for production of cephalosporins. More particularly, this invention relates to a new method for production of a cephalosporin ester of the following general formula (I), which is characterized by reacting a derivative of an organic acid of the following general formula (II) with a 7-aminocephem compound of the following general formula (III) in the presence of an enzyme of a microorganism of one of the genera Escherichia, Bacillus, Proteus and Pseudomonas which is able to synthesize a cephalosporin ester of general formula (I) from a derivative of an organic acid of general formula (II) and 7-aminocephem-4-carboxylic acid of general formula (III):

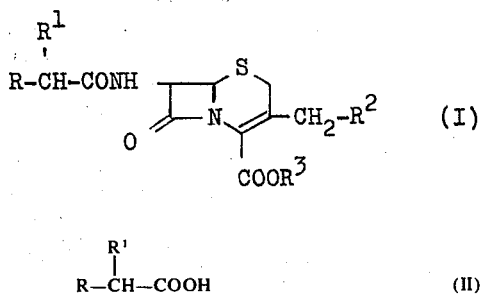

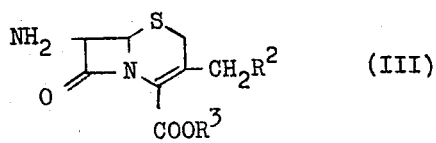

wherein R is an unsaturated six-membered carbocyclic ring or five-mentioned heterocyclic ring residue which may optionally have uncharged substituent groups; $R_1$ is hydrogen or an uncharged substituent group such as hydroxyl or halogen, $R^2$ is a hydrogen atom or an organic group which is bound through an oxygen, sulfur or nitrogen atom; $COOR^3$ is a group which may easily be converted to COOH and, for convenience' sake, will hereafter be called an ester residue.

Heretofore, the production of semi-synthetic cephalosporins through the condensation reactions of reactive derivatives of organic acids (II) with 7-aminocephem-4-carboxylic acids has been invariably carried out by chemical procedures. However, these chemical procedures are more or less accompanied with drawbacks. For example, in the acylation of a 7-aminocephem-4-carboxylic acid with an acyl halide which is a typical acylating agent, the reaction has been carried out by using the acyl halide at least in equimolar amount relative to the 7-aminocephem-4-carboxylic acid, but when the acyl halide, which is highly reactive per se, is employed in excess, unstable 7-aminocephem-4-carboxylic acid partially undergoes an undesirable side reaction which results in reduced yields. And it is very difficult to control reaction conditions so as to suppress the side reaction to a minimum.

We conducted extensive studies to establish a better process for production of semi-synthetic cephalosporins and discovered that an enzymatic condensation reaction can be utilized in the production of cephalosporins from organic acid (II) or a derivative thereof and 7-aminocephem-4-carboxylic acid.

Thus, we found that, as will be seen from Reference Example 1 which appears hereinafter, there are among bacteria of the genera of Escherichia, Bacillus, Proteus and Pseudomonas the organisms which are able to synthesize cephalosporins (I'), which correspond to said general formula (I) wherein $R^3$ is a hydrogen atom, from an organic acid of general formula (II) or a derivative thereof and a 7-aminocephem-4-carboxylic acid (III') which corresponds to said general formula (III) wherein $R^3$ is a hydrogen atom. Further studies led to the finding that the bacterial enzymes which catalyze the reactions have an extremely high activity to hydrolyze the product cephalosporins (I') into (II) and (III') and that these synthetic reactions proceed by far faster when a derivative of organic acid (II) is used than when orgaic acid (II) as such is used as the acylating agent. Thus, these bacterial enzymes, when organic acid (II) is used as an acyl doner, catalyze the following reversible reaction and, as shown in Reference Example 2 which appears hereinafter, the equilibrium-constant (K) is much smaller than unity (see Table II). This shows the rate of hydrolysis of (I') is considerably greater than the rate of production of (I').

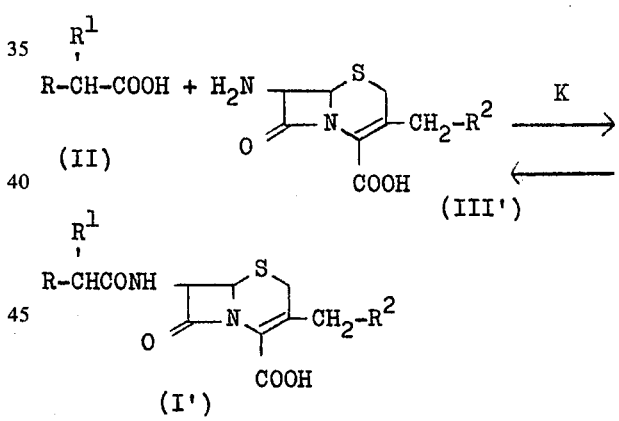

(wherein R, $R^1$ and $R^2$ have the same meaning as defined above.)

When a derivative of organic acid (II), e.g. a glycine derivative, is employed instead of the acid (II), the rate of synthesis of (I') is considerably increased to the extent that it is substantially equal to the rate of hydrolysis of (I'). (See Reference Example 3 hereafter.) However, the organic acid derivative is readily hydrolyzed into (II) and glycine by these enzymes besides its being used in the above condensation reaction. Even if high concentration of the organic acid derivative is employed in order that (I') would be accumulated beyond the equilibrium point of the above reaction formula, the compound (I') once accumulated is rehydrolyzed as the organic acid derivative and (III') are reduced in amount. Thus, it was found difficult to allow (I') to be accumulated in a high concentration over the equilibrium concentration (Reference Example 3).

However, we have surprisingly discovered that rate of formation of (I) from a derivative of (II) and (III)) is about equal to that of formation of (I') from a derivative of (II) and (III'), that (I) once produced is not hydrolyzed at all no matter how much is the reaction time protracted and that, consequently, (I) can be obtained from (II) and (III) in a high yield.

As is well known, microbial enzymes have strict substrate-specificity and, therefore, the enzymatic production of (I) from a derivative of (II) and (III) can not be expected to even the skilled in the art from the fact that (I') can be produced from a derivative of (II) and (III'). Moreover, it is surprising that the formation rate of (I) from a derivative of (II) and (III) is about equal to that of (I') from a derivative of (II) and (III').

Furthermore, most enzymes are known to be inhibited by a large excess of substrate as is called "substrate-inhibition". In hitherto-known enzymatic production of penicillins and cephalosporins, concentration of substrate has been about 0.1 to 1 %. In the present invention, however, "substrate-inhibition" does not occur at all even if the concentration of substrate is more than 10 % and the enzymatic reaction proceeds smoothly.

As mentioned above, penicillin-synthesizing enzyme has, in general, a strong activity of hydrolyzing penicillin. Therefore, the penicillin once produced is hydrolyzed when reaction time is protracted [Biochemical Journal 115, 759-761(1969)]. On the other hand, in this invention, the hydrolysis of the product (I) does not occur at all and (I) is obtainable in remarkably high yield of 70–80%.

Another surprising discovery was that it was even possible to synthesize (I) in high yield by employing (III) in a concentration ten times that of (III') when (III) is of highly water-soluble type.

These findings were followed by further studies which have culminated in the present invention. The advantages of the method of this invention will become more apparent if one compare it with the above-described method involving the same organism, that is the method utilizing the synthetic reaction of (I') from a derivative of (II) and (III'). Thus, (1) the production yield of the desired compound is remarkably high; (2) the reaction can be conducted in high concentration without inducing reduction in production yield, (3) the proportion of a derivative of organic acid (II) may be far less than the amount required in the above-mentioned method where (III') is used, and (4) since the accumulation of product compound (I) is not significantly reduced no matter how much is the reaction time protracted, the end-point of the reaction is not critical.

Aside from the above-mentioned advantages, there is the advantage that because, unlike (I'), the product compound (I) is sparingly soluble in water, it can be purified by extraction with organic solvents and, accordingly, the product can be easily obtained in a high purity that permits its use as injections. This is also a major advantage of this method over the above-mentioned method whose contemplated product is (I').

The bacteria to be exploited in this application can be selected from among the strains of microorganisms in deposit of various type culture collections or may be separated from by natural kingdom including the soil, sewages, marine water, human and animal excreta, atmosphere and other sources. Among these bacteria are many strains which elaborate $\beta$-lactamases. When the particular $\beta$-lactamase acts upon at least one of 7-aminocephem-4-carboxylic acid ester (III) and cephalosporin ester (I), it is preferable to grow and use a non-$\beta$-lactamase-producing variant in the per se conventional manner.

All the mutant strains that can be induced by conventional techniques for the purpose of enhancing the desired cephalosporin-synthetic activity can also be employed to advantage in the practice of this invention. Below given is a method of screening and selecting the strains which can be utilized according to this invention.

Method of selecting the useful strains:

A test bacterium is shake-cultured at a suitable temperature in the range of 20° to 40°C for 1 to 2 days.

After adequate growth has been attained, the cells are separated and suspended in a volume of citrate-phosphate buffer (0.05M, pH 6.0) which is equal to the volume of the culture. Then, 20 mM of 7-aminocephalosporanic acid (hereinafter abbreviated as 7-ACA) and 60 mM of 2-thienylacetylglycine (hereinafter abbreviated as (TAG) are added, and the reaction is conducted at 37°C for 30 minutes. The strain which accumulates not less than 2mM of 7-thienylacetamidocephalosporanic acid (hereinafter abbreviated as CET or cephalothin) is selected as one of the strains which are useful for the purposes of this invention. The yield of CET is determined by spectropolarimetry. Thus, the change ($\Delta R_D$) in optical rotation reading at 589 m$\mu$ (10 cm, 27°C, pH 6.0) that is encountered when 20 mM of 7-ACA has been 100 % converted to CET is 0.540. To measure the yield of CET by taking advantage of this fact, the following procedure is employed. The reaction mixture is first cooled to 0°C and then centrifuged to remove the cells. The optical rotation ($R_D^{30}$) of the resultant supernatant fluid is measured with a Perkin-Elmer Model 141 digital polarimeter (at 27°C) and, from the deviation from the pre-reaction rotation ($R_D^0$), the yield of CET is calculated by means of the following equation.

$$\text{Yield of } CET = \frac{R_D^{30} - R_D^0}{\Delta R_D} \times 20 \ (mM)$$

Some exemplary strains which have been selected by the foregoing procedure from among the strains in deposit at various type culture collections are as follows

*Escherichia coli* IFO-3542, *Escherichia coli* ATCC-9637, *Escherichia coli* var. *communior* IFO-3547, *Escherichia coli* var. *communior* IFO-3548, *Bacillus sp.* ATCC-14552, *Proteus rettgeri* ATCC-9250, *Escherichia coli* IFO-13502(ATCC-21985), *Escherichia coli* IFO-3470(ATCC-21986), *Escherichia coli* IFO-3450(ATCC-21987), *Pseudomonas putida* IFO- 3537(ATCC-21988) and *Bacillus sp.* IFO-12063(ATCC-21989).

The IFO and ATCC numbers indicate the accession numbers of the organisms at the Institute for Fermentation, Osaka, Japan and at American Type Culture Collection, Rockville, Md, U.S.A., respectively.

To produce the desired cephalosporin ester (I) using a bacterium which has the above-described ability to synthesize cephalosporin esters (I), the microorganism is usually first cultivated and the resultant culture or a processed matter thereof is then contacted with a derivative of organic acid (II) and 7-aminocephem-4-carboxylic acid ester (III) under suitable conditions.

The cultural method for obtaining said culture may be whichever of aerated stirring culture, shake culture and stationary culture, though aerobic culture is usually preferred. The culture medium may be any one or a combination of two or more of nutritive materials which are routinely employed, e.g. meat extract, yeast extract, peptone, casein hydrolyzate, corn steep liquor, etc. and, if necessary, may be supplemented with phenylacetic acid, such carbon compounds as sugars, organic acids, n-paraffins, etc., various inorganic and organic nitrogenous compounds including nitrogen in amino or nitrate form, phosphates, magnesium salts, sodium chloride and other metallic ions, various vitamins, etc. The medium is adjusted to pH 6 to 9 before use. The incubation temperature is desirably in the range of 20 to 37°C.

While the cultivation time depends upon the particular strain of bacterium and cultural conditions, particularly the cultural equipment, medium composition, incubation temperature, etc., it is advisable to terminate the cultivation when the cephalosporin ester-synthesizing activity of the enzyme system is maximal, i.e. somewhere between the second half of the logarithmic phase of growth and the first half of the stationary phase. Usually, the time of 8 to 48 hours proves adequate.

The culture thus obtained or a processed matter thereof is used in the reaction of synthesizing cephalosporin ester. The term "processed matter" as used herein means any and all matters which have been obtained by processing the said culture somehow into forms which have an improved cephalosporin ester-synthesizing activity and which are more suited ot the production of cephalosporin esters. For example, when said synthesizing activity occurs intracellularly, the processed matter includes, among others, (1) the cells separated from the bacterial culture, (2) the cell-free extract having the cephalosporin ester-synthesizing enzyme activity which has been obtained by the application of some known treatment to the bacterial cells, (3) the partially or completely purified cephalosporin ester synthesizing enzyme which is prepared from said cell-free extract by some known procedure, and (4) water-insoluble enzymes having cephalosporin ester-synthesizing activity which are prepared by causing said partially or completely purified enzyme to be bound to a water-insoluble high molecular material either physically or chemically. When said synthetic activity occurs extracellularly, the processed matter means any of (1) the supernatant fluid obtained after the cells is removed from the culture, (2) the partially or completely purified cephalosporin ester-synthesizing activity which is obtained by subjecting said supernatant to some known enzyme purification procedure, and (3) the cephalosporin ester-synthesizing activity which has been prepared as above and bound to a water-insoluble high molecular support material either physically or chemically.

In producing cephalosporin ester (I) from a derivative of organic acid (II) and 7-aminocephem-4-carboxylic acid ester (III) with the aid of said culture or processed matter, the desired condensation reaction is usually conducted in aqueous solution. In this connection, the pH of the reaction system is preferably controlled between pH 4and pH 10 and, for better results, between pH 6 and pH 9. When the culture or processed matter is water-soluble, the above condensation reaction is conducted in solution, but when the culture or processed matter is water-insoluble, the condensation reaction is conducted either in suspension or in the following manner. Thus, a derivative of the said water-insoluble cephalosporin ester-synthesizing enzyme is packed into a column and an aqueous solution containing said derivative of organic acid (II) and said 7-aminocephem-4-carboxylic acid ester (III) is passed through the column so that the condensation reaction may take place within the column. In conducting the condensation reaction in any of the described manners, it is possible to improve the reaction yield by adding a water-miscible organic solvent, e.g. alcohols, acetone or dimethylsulfoxide, to the reaction system. The reaction time varies with the concentrations of the substrates, the activity of the cephalosporin ester-synthesizing enzyme, the reaction temperature and other factors, but it in general ranges from 1 minute to 30 hours.

The reaction temperature is selected from the range of about 0° to about 50°C. The concentrations of substrates are determined chiefly with reference to the cephalosporin ester-synthesizing activity. Generally speaking, the concentration of 7-aminocephem-4-carboxylic acid ester (III) is selected from the range of 0.1 to 20 percent.

In order to enhance the production yield of cephalosporin ester (I) relative to 7-aminocephem-4-carboxylic acid ester (III), the concentration of a derivative of organic acid (II) is preferably at least not less than equimolar with respect to 7-aminocephem-4-carboxylic acid ester (III).

Referring to general formula (II), the uncharged unsaturated carbocyclic six-membered residue or heterocyclic five-membered ring residue R is exemplified by phenyl, cyclohexenyl, cyclohexadienyl, thienyl, buryl, etc. The substituent groups that may be possessed by these cyclic groups are exemplified by —OH, —SH, —$NO_2$, halogen (e.g. —Cl, —Br), an alkyl (e.g. —$CH_3$, —$C_2H_5$), an alkoxy (e.g. —$OCH_3$, —$OC_2H_5$), —CN and so on. In general formula (II), $R^1$ is not a charged group such as amino or carboxyl but an uncharged group such as, for example, hydrogen, hydroxyl or halogen (e.g. —Cl, —Br). Thus, examples of organic acid (II) include, among others, phenylacetic acid, mandelic acid, cyclohexadienylacetic acid, α-oxycyclohexadienyl-acetic acid, cyclohexenylacetic acid, 2-thienylacetic acid, 2-furylacetic acid, parahydroxyphenylacetic acid, paramercaptophenylacetic acid, paranitrophenylacetic acid, parachlorophenylacetic acid, parabromophenylacetic acid, paramethylphenylacetic acid, paraethylphenylacetic acid, paramethoxyphenylacetic acid, paracyanophenylacetic acid and so on.

While the above examples of phenylacetic acid are relevant to para-substitutions only, it should of course be understood that compounds wherein similar substituents occur in the ortho- or meta-position are also useful. Furthermore, compounds wherein two or more substituents, either the same or different in kind, occur on the ring are also included in organic acid (II).

The derivative of said organic acid (II) means the compounds which can be hydrolyzed in aqueous medium by the enzyme of the microorganism employed in accordance with this invention to give organic acid (II). Preferred example include, among others, such water-soluble derivatives as amino acid derivatives, particularly the corresponding glycine derivatives, e.g. N-phenylacetylglycine, N-(2-thienylacetyl)glycine, etc.; glycolic acid derivatives; the thioglycolic acid derivative of said organic acid and the amides of said organic acid. Besides them, an alkyl ester, e.g. methyl ester, ethyl ester, of the organic acid may at times be employed.

The organic group whose available valence is bound through O, S or N as denoted by symbol $R^2$ in general formula (III) is exemplified by alkoxy (e.g. —OCH$_3$, —OC$_2$H$_5$), alkylcarbonyloxy (e.g. —OCOCH$_3$, OCOC$_2$H$_5$),

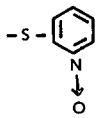

pyridylthio(e.g. 2-pyridylthio), pyridinium (e.g.

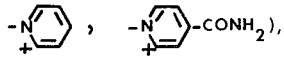

alkylthiocarbonyloxy(e.g. —OCOSCH$_3$, —OCOSC$_2$H$_5$), dialkylaminothiocarbonylthio(—SCSN(CH$_3$)$_2$, —SCSN(C$_2$H$_5$)$_2$, trialkylammonium (e.g. —N$^+$(CH$_3$)$_3$), —N$_3$, aralkyloxycarbonylamino (e.g.

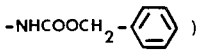

pyridazinylthio-N-oxide(e.g. 3-methylpyridazinylthio-2-oxide, 3-methoxypyridazinylthio-1-oxide) and so on.

The ester residue represented by $R^3$ in —COOR$^3$ may be a group which can be easily converted to —COOH by treatment with alkali, acid or enzyme or by reduction, examples including halogenoalkyl (e.g. trichloroethyl), alkyl- or arylsulfonylalkyl(e.g. methylsulfonylethyl, ethylsulfonylethyl, phenylsulfonylethyl), alkyl (e.g. methyl, ethyl), alkoxyalkyl (e.g. methoxymethyl), alkylcarbonylalkyl (e.g. acetonyl), diarylalkyl(e.g. diphenylmethyl), alkylthioalkyl (e.g. methylthiomethyl), alkyl- or arylsulfinylalkyl (e.g. methylsulfinylethyl, phenylsulfinylmethyl) and so on. The "alkyl" herein referred to is typically exemplified by one having 1 to 4 carbon atoms such as methyl, ethyl, propyl, isopropyl, butyl, isobutyl, sec. butyl, tert. butyl and the "aryl" is typically exemplified by phenyl which may be substituted by alkyl, alkoxy, halogen, etc. Therefore, said 7-aminocephem-4-carboxylic acid ester (III) includes such species as 7-aminocephalosporanic acid methoxymethyl ester, 7-amino-3-desacetoxycephalosporanic acid methylsulfonylethyl ester, 7-amino-3-methoxymethyl-3-cephem-4-carboxylic acid methoxymethyl ester, 7-amino-3-{2-(1-oxopyridyl)thiomethyl}-3-cephem-4-carboxylic acid diphenylmethyl ester, 7-amino-3-(1-pyridylmethyl)-3-cephem-4-carboxylic acid methoxymethyl ester, 7-amino-3-{1-(4-carboxamidopyridyl)-methyl}-3-cephem-4-carboxylic acid methoxymethyl ester, 7-amino-3-methylthiocarboxymethyl-3-cephem-4-carboxylic acid methoxymethyl ester, 7-amino-3-trimethylaminomethyl-3-cephem-4-carboxylic acid acetonyl ester, 7-amino-3-dimethyldithiocarbamylmethyl-3-cephem-4-carboxylic acid diphenylmethyl ester, 7-amino-3-azidomethyl-3-cephem-4-carboxylic acid methoxymethyl ester, 7-amino-3-benzyloxycarbonylaminomethyl-3-cephem-4-carboxylic acid methoxymethyl ester and so on.

There are new compounds among these, 7-aminocephem-4-carboxylic acid esters which can be produced by one of the procedures described below.

1. The method in which the alcohol ($R_3$OH) corresponding to the desired ester residue or a reactive derivative thereof is reacted with penicillin G or penicillin V to obtain the corresponding penicillin G ester or penicillin V ester which is then caused to undergo a ring-enlarging reaction in the per se conventional manner and the 7-position of the resultant corresponding 7-acyl-3-desacetoxycephalosporanic acid ester is deacylated to obtain the desired 7-amino-3-desacetoxycephalosporanic acid ester;

2. The method in which, after the amino group of cephalosporin C has been protected, the material compound is reacted with the alcohol corresponding to the desired ester residue or a reactive derivative of said alcohol to obtain cephalosporin C ester and, then, the 7-acyl group of the same compound is removed in the conventional manner to obtain the desired 7-aminocephalosporanic acid ester; and 3. The method in which, after the 3-position of cephalosporin C has been modified as required, the procedure of method (2) is followed to obtain the desired 7-aminocephem-4-carboxylic acid ester.

The cephalosporin ester (I) thus synthesized from a derivative of organic acid (II) and 7-aminocephem-4-carboxylic acid ester (III) in the presence of said bacterial culture or processed matter thereof can be isolated and purified under mild conditions from the reaction mixture by conventional procedures such as extraction with an organic solvent which will form a distinct phase with respect to water, crystallization from a suitable solvent or chromatography, or by means of an oraganic acid which is capable of forming an insoluble salt with cephalosporin compound (I).

Cephalosporin ester (I) thus obtained includes useful compounds which are antibiotic per se, it is generally as important as (I') in the sense that includes intermediates which can be easily converted to (I') which includes still more desirable drugs.

Throughout the specification, the abbreviation "g", "mg.", "mμ", "ml.", "l.", "°C", "M", "mM", "ppm", "r.p.m.", "psi" and "N" respectively refer to "gram(s)", "milligram(s)", "millimicron(s)", "milliliter(s)", "liter(s)", "degree centigrade", "molar concentration", "millimolar concentration", "part(s) per million", "revolution per minute", "pound(s) per square inch" and "normality"; percent(%)

regarding concentrations is weight per volume, i.e. "gram per deciliter", unless otherwise specified.

Below given are the compositions of the media employed in the reference examples and working examples which appear hereafter.

| (Medium A) | |
| --- | --- |
| Meat extract | 10 g. |
| Peptone | 10 g. |
| NaCl | 5 g. |
| Tap water | 1l., pH 7.0 |
| (Medium B) | |
| Sodium glutamate | 20 g. |
| Yeast extract | 10 g. |
| Phenylacetic acid | 2 g. |
| NaCl | 2 g. |
| $KH_2PO_4$ | 1 g. |
| $MgSO_4 \cdot 7H_2O$ | 0.2 g. |
| Tap water | 1l., pH 7.0 |
| (Medium C) | |
| Meat extract | 10 g. |
| Peptone | 10 g. |
| NaCl | 5 g. |
| Benzoic acid | 1 g. |
| Tap water | 1l., pH 7.0 |

REFERENCE EXAMPLE 1

A loopful of *Escherichia coli* IFO-3542, *Pseudomonas putida* IFO-3537, *Bacillus sp.* IFO-3860 or *Proteus rettgeri* ATCC-9250 from a 2-day slant culture was used to inoculate 20 ml. of medium B (for Escherichia) or medium C (for other organisms) in a conical flask of 200 ml. capacity, where it was cultivated under shaking at 24°C (for Escherichia) or 28°C for 24 hours. The resultant cultures of strains used, except the culture of the Bacillus, were centrifuged to harvest the cells, which were suspended in 5 ml. of 0.2M citrate-phosphate buffer (pH 6.0). As to the Bacillus, its culture broth was directly subjected to the following experiment. To each of the cell suspensions, there was added 5 ml. of an aqueous solution (pH 6.0) containing 10 mg./ml. of 7-ACA and 40 mg./ml. of TAG. The reaction was allowed to proceed at 37°C for 4 hours. The quantitative determination of the product cephalothin (CET) was performed by the spectrophotometric method [Journal of the American Chemical Society, 94, 4035, (1972)] which measures cephalosporins selectively even in the concomitant presence of 7-ACA from the decrease in absorbance at 260 mµ after treatment with β-lactamase produced by Aerobacter cloaseae IFO-12937. The results are set forth in the following table.

Table 1

| Microorganism | Production yield(%) of cephalothin |
| --- | --- |
| *Escherichia coli* IFO-3542 | 46 |
| *Pseudomonas putida* IFO-3537 | 41 |
| *Bacillus sp.* ATCC-14552 | 37 |
| *Proteus rettgeri* ATCC-9250 | 20 |

REFERENCE EXAMPLE 2

The entire growth of a slant culture (28°C, 24 hours' cultivation, medium A) of *Escherichia coli* IFO-13502 was suspended in 10 ml. of sterile water and the resultant suspension was used to inoculate 400 ml. of medium B in a shake flask of 2-liter capacity. The inoculated medium was incubated under shaking at 24°C for 24 hours. The resultant culture was centrifuged to harvest the cells, which were suspended in 20 ml. of distilled water. Meanwhile, there were prepared 5 ml. each of aqueous solutions containing 40 mM of cephalothin and 0, 40, 120 or 280 mM of thienylacetic acid (hereinafter abbreviated as TA).

Each of the solutions was added to a 5 ml. portion of the above cell suspension and the mixture was held at pH 6.0 and 37°C to allow the hydrolysis of cephalothin to take place. The pH of the reaction system was exactly maintained at 6.0 with the aid of a pH-stat. The concentration of cephalothin and that of 7-ACA when the reaction had established an equilibrium were measured by spectrometric and polarimetric methods.

The results, together with the times that elapsed before the equilibria were reached, are set forth below in the table. In this connection, equilibria were also established when cephalothin was synthesized from 7-ACA and TA and the mole ratio of cephalothin to 7-ACA at the equilibrium was directed by the mole ratio used of 7-ACA at the equilibrium was directed by the mole ratio used of 7-ACA and TA and substantially coincided with the mole ratio of cephalothin to 7-ACA found in the cephalothin hydrolysis experiment. It should be noted that, in the above comparison, the value for cephalothin was arrived at on the basis of equimolar amounts of TA and 7-ACA.

Since the synthesis from TA and 7-ACA requires a long time before it establishes an equilibrium, the data tabulated below refer only to the values obtained from the hydrolysis of cephalothin. It will be seen from Table II that if cephalothin be synthesized from 20 mM of 7-ACA and 160 mM of TA, the yield of cephalothin is as low as 30 percent.

If the substrate concentration of the reaction system be increased, the production yield of cephalothin at the equilibrium point will be somewhat increased but since the solubility of 7-ACA is low, any significant effect can be expected even if the concentration is increased to 50 mM or more.

Table II

| Concentration of TA and CET at start of reaction (mM) | | Concentration of TA and 7-ACA (mM) | | Concentration of CET and 7-ACA at equilibrium (mM) | | Time before the equilibrium is established (hour) |
| --- | --- | --- | --- | --- | --- | --- |
| TA | CET | TA | 7-ACA | CET | 7-ACA | |
| 0 | 20 | 20 | 20 | 0.9 | 19.1 | 0.5 |
| 20 | 20 | 40 | 20 | 1.2 | 18.8 | 1 |
| 60 | 20 | 80 | 20 | 2.1 | 17.9 | 2 |
| 140 | 20 | 160 | 20 | 6.0 | 14.0 | 4 |

REFERENCE EXAMPLE 3

The washed cells of *Escherichia coli* IFO-13502 which had been prepared in the same manner as Reference Example 2 were suspended in distilled water to give a concentration ten times that of the original culture broth and while the suspension was held at ph 6.0 by means of a pH-stat, the rates of the following reactions were measured at 37°C. (1) The rate of synthesis of cephalothin from TA(80mM) and 7-ACA (20mM); (2) the rate of synthesis of cephalothin from TAG (80 mM) and 7-ACA (20 mM); (3) the rate of hydrolysis of cephalothin (20 mM) (production of TA and 7-ACA); and (4) the rate of hydrolysis of TAG (80 mM) (the production of TA and glycine). The rates of reactions (1), (2) and (3) were measured by spectrophotometry. The rate of reaction (4) was determined by titrating the glycine produced with ninhydrin [Analyst, 80, 209, (1955)]. The results are set forth in Table III, from which it will be seen that the rate of production of cephalothin from TAG and 7-ACA is about 7 times as high as the rate of production of the same from TA and 7-ACA and approaches the rate of hydrolysis of cephalothin and also that the rate of hydrolysis of cephalothin by the present bacterium is by far higher than the rate of synthesis of cephalothin. From these figures, it will be seen that if the particular organism is allowed to synthesize cephalothin from TAG (160 mM) and 7-ACA (40 mM), the rate of synthesis of cephalothin will be equal to the rate of its hydrolysis when about 20 mM of cephalothin has just been produced, that is to say the net production rate (accumulation rate) of cephalothin becomes nil(zero) at that moment.

As the concentration of TAG drops, the accumulation rate of cephalothin becomes negative. Therefore, though the accumulation of cephalothin exceeds by far the maximal accumulation of cephalothin from TA(160 mM) and 7-ACA(40 mM) (the accumulation of cephalothin at equilibrium), it will still be 20 mM (50% conversion rate) at best.

EXAMPLE 1

The cells of Escherichia coli IFO-13502 from four slants (medium A containing agar 2 %) grown at 28°C for 24 hours were suspended in 40 ml. of physiological saline and 10 ml. portions of the suspension were inoculated into 2-liter shake flasks containing 500 ml. of medium B each. The flasks were incubated under shaking at 24°C for 24 hours to prepare a seed culture. A 2-liter portion of the seed culture was then used to inoculate 100 l. of medium B (containing 0.005 % of an antifoam) in a tank of 200-liter capacity and incubated with sparging and agitation for 24 hours. The conditions were 50 % aeration, 150 r.p.m. and 24°C. After the cultivation, the wet cells were harvested by a centrifugal separator and suspended in 5 l. of pure water. After the cells had been thoroughly washed, the suspension was re-centrifuged to obtain about 1100 g. of wet cells. The cells were resuspended in 5 l. of pure water and kept in lyophile state till use.

The washed cells thus prepared were suspended in 10 ml. of 0.5 M citrate-phosphate buffer to give a concentration ten times that of the original culture broth.

To this suspension was added 10 ml. of a buffer solution similar to the above containing 160 mM of mandelylglycine and 80 mM of 7-amino-3-desacetoxycephalosporanic acid (hereinafter abbreviated as 7-ADCA) methylsulfonylethyl ester. The mixture was allowed to react at 37°C for 4 hours with constant agitation, whereupon 27.5 mM of 7-{α-phenyl-α-hydroxyacetamido}-3-desacetoxycephalosporanic acid methylsulfonylethyl ester accumulated in the reaction system. The quantitative determination was performed by polarimetry.

EXAMPLE 2

The washed cells of Escherichia coli IFO-13502 which had been prepared according to Example 1 were suspended in 0.2 M citrate-phosphate buffer (pH 6.0) to give a concentration ten times that of the culture broth. Meanwhile, phenylacetylglycine (hereinafter abbreviated as PAG) and 7-ADCA or 7-ADCA methyl sulfonylethyl ester were dissolved in the same buffer solution and the solution was pooled with the above cell suspensions. The mixture was then allowed to react at 37°C with agitation. The concentrations of cells, PAG, 7-ADCA and 7-ADCA methylsulfonylethyl ester in the reaction mixture are shown in Table IV. In the table, the asterisk(*) means that the cell concentration of the culture broth was used as standard.

Table III

| Substrates (mM) | Compound determined | Value found (mM) at various intervals (in minutes after start of reaction) | | | | | | | | Reaction rate ($\mu$ moles/min.) |
|---|---|---|---|---|---|---|---|---|---|---|
| | | 5 | 10 | 20 | 30 | 60 | 90 | 120 | 150 | |
| TA(80)+7-ACA(20) | CET (produced) | 0.54 | 0.83 | 1.23 | 1.49 | 2.01 | 2.16 | | 2.53 | 0.05 |
| TAG(20)+7-ACA(20) | CET (produced) | 2.32 | 3.31 | 3.23 | 2.42 | 1.25 | 1.10 | 1.01 | | 0.36 |
| TAG(80)+7-ACA(20) | CET (produced) | 2.33 | 4.14 | 6.42 | 7.28 | 5.53 | 4.31 | 3.55 | | 0.36 |
| CET (18) | CET (disappeared) | 15.92 | 13.50 | 10.58 | 8.78 | | | | | 0.36 |
| TAG (80) | Gly* (produced) | 19.40 | 25.10 | 45.82 | 59.23 | 74.93 | | | | 2.29 |

*Gly : Glycine

Table IV

| Exp. No. | Cell Concentration | Concentration of PAG(mM) | Concentration of 7-ADCA(mM) | Concentration of 7-ADCA ester (mM) |
|---|---|---|---|---|
| 1 | X 5* | 80 | 40 | 0 |
| 2 | X 2 | 80 | 0 | 40 |
| 3 | X 5 | 160 | 80 | 0 |
| 4 | X 2 | 160 | 0 | 80 |
| 5 | X 5 | 240 | 120 | 0 |
| 6 | X 2 | 240 | 0 | 120 |

The amount of 7-phenylacetamido-3-desacetoxycephalosporanic acid produced from PAG and 7-ADCA was determined by spectrophotometry as applied in combination with the use of β-lactamase. To determine the amount of 7-phenylacetamidocephalosporanic acid methylsulfonylethyl ester produced from PAG and 7-ADCA methylsulfonylethyl ester, tetrahydrofuran was added to the reaction mixture and, after centrifugation to remove the cells, the supernatant was subjected to the above-mentioned polarimetric measurement. The results are set forth in Table V.

Table V

| | Yield of cephalosporin at various intervals (minutes after start of reaction) (mM) | | | | | | | Max. conversion (%) | Conversion at end of reaction (%) |
| --- | --- | --- | --- | --- | --- | --- | --- | --- | --- |
| Exp. No. | 15 | 60 | 90 | 120 | 180 | 240 | 20×60 | | |
| 1 | 7.4 | 9.7 | 10.1 | 9.2 | 10.0 | 8.7 | 8.0 | 25 | 20 |
| 2 | 16.6 | 24.4 | 25.0 | 25.3 | 26.2 | 26.5 | 27.4 | 68 | 68 |
| 3 | 11.0 | 15.1 | 22.3 | 22.1 | 23.1 | 22.5 | 20.2 | 29 | 25 |
| 4 | 19.4 | 51.3 | 56.0 | 56.2 | 56.4 | 57.4 | 58.0 | 73 | 73 |
| 5 | 10.5 | 25.0 | 30.6 | 34.2 | 37.0 | 32.4 | 31.3 | 31 | 26 |
| 6 | 18.1 | 49.0 | 59.0 | 67.7 | 78.0 | 85.2 | 91.2 | 76 | 76 |

Whereas the convention ratio of 7-ADCA into cephalosporin was 25 to 31 %, that 7-ADCA ester into cephalosporin ester was 68 to 76 %. The product was identified in the following matter. To the 20-hour reaction mixture of Experiment 6(containing 91 mM of cephalosporin ester) was added five times its volume of tetrahydrofuran to dissolve the product thoroughly and, then, the cells and insoluble proteins were removed by centrifugation. The resultant supernatant fluid was concentrated under reduced pressure at a temperature not exceeding 35°C. After the tetrahydrofuran had been distilled off, crystals separated out. The crystals were harvested by filtration, washed well with water and recrystallized from methanol. The procedure yielded crystals of 7phenylacetamido-3-desacetoxycephalosporanic acid methylsulfonylethyl ester, melting point: 145°–146°C, $[\alpha]_D^{25}$ +78°(c=1.0, $CH_2Cl_2$), $E_{1cm}^{1\%}$ (260 m$\mu$)=159(Yield 72 %). The product was identified with an authentic sample by NMR and IR spectrometry.

EXAMPLE 3

There was prepared an aqueous solution (pH 6.0) containing PAG and 7-ADCA methylsulfonylethyl ester. Then, a given amount of the washed cells of Escherichia coli IFO-13502 according to Example 1 was suspended inn an equal volume of distilled water. The suspension was added to the above aqueous solution and the mixture was allowed to react at 37°C while its pH was maintained at 6.0 with 2N HCl by means of pH-stat. The concentrations of cells and substrates in the reaction mixture are indicated in Table VI. The progress of the reaction is as shown in Table VII. The quantitative analysis of the reaction product (7-phenylacetamido-3-desacetoxycephalosporanic acid methylsulfonyethyl ester) was performed in the manner described in Example 2.

Table VI

| Exp. No. | Concentration of cells | Concentration of PAG | Concentration of 7-ADCA ester |
| --- | --- | --- | --- |
| 1 | 5 Times | 480 mM | 240 mM |
| 2 | 8.5 Times | 660 mM | 330 mM |

Table VII

| | Yield of cephalosporin ester at various reaction periods (minutes) (mM) | | | | | | | Reaction Yield (%) |
| --- | --- | --- | --- | --- | --- | --- | --- | --- |
| Exp. No. | 15 | 60 | 90 | 120 | 180 | 240 | 7×60 | |
| 1 | 18 | 38 | 49 | 62 | 93 | 124 | 172 | 72 |
| 2 | 18 | 60 | 88 | 119 | 152 | 210 | 260 | 79 |

EXAMPLE 4

A loopful of Escherichia coli IFO-3450, Escherichia coli IFO-3470 or Escherichia coli var. communior IFO-3547 from a 2-day slant culture was used to inoculate 20 ml. of medium B in a shake flask of 200 ml. capacity and cultivated under shaking at 24°C for 24 hours. The cells thus grown were harvested by centrifugation and suspended in 2.5 ml. of 0.2 M citrate-phosphate buffer (pH 6.0). To this suspension was added 2.5 ml. of a similar buffer containing 480 mM of PAG and 240 mM of 7-ADCA methylsulfonylethyl ester and the mixture was allowed to react under shaking at 37°C for 16 hours.

Then, 25 ml. of tetrahydrofuran was added to the reaction mixture to completely dissolve the products and the bacterial cells and insoluble proteins were removed by centrifugation. The resultant supernatant was then subjected to a polarimetric determination to measure the yield of 7-phenylacetamido-3-desacetoxycephalosporanic acid methylsulfonylethyl ester. The results are shown in Table VIII.

Table VIII

| Microorganism | Yield (mM) of the contemplated product (cephalosporin ester) |
| --- | --- |
| Escherichia coli IFO-3450 | 94.8 mM(79 % theoretical) |
| Escherichia coli IFO-3470 | 99.6 mM(83 % theoretical) |
| Escherichia coli var. communior IFO-3547 | 82.8 mM(69 % theoretical) |

EXAMPLE 5

A loopful of Bacillus sp. ATCC-14552 or Bacillus sp. IFO-12063 from a 2-day slant culture was used to inoculate 20 ml. of medium C in a shake flask of 200 ml. capacity and cultivated under shaking at 28°C for 24 hours. To each of the resultant cultures was added a solution of 160 mg. of TAG in 2.5 ml. of 0.5 M-citrate-phosphate buffer (pH 6.0), followed by the addition of 114 mg. of 7-ADCA as methyl ester dissolved in 2.5 ml. of methanol.

The reaction was allowed to proceed at 37°C with constant stirring for 16 hours. The amount of 7-(2'-thienylacetamido)-3-desacetoxycephalosporanic acid methyl ester as accumulated in the reaction system was 16.2 mM when the culture of Bacillus sp. ATCC-14552 was used or 15.8 mM in the case of Bacillus sp. IFO-12063. The determinations were made by spectrophotometry as applied in combination with the use of $\beta$-lactamase.

EXAMPLE 6

A loopful of Pseudomonas putida IFO-3537 or Proteus rettgeri ATCC-9250 from a 2-day slant culture was used to inoculate 40 ml. of medium C in a shake flask of 200 ml. capacity and cultivated under shaking at 28°C for 24 hours. The cells thus grown were harvested by centrifugation and suspended in 2 ml. of 0.2M citrate-phosphate buffer (pH 6.0). To this suspension was added 2 ml. of a similar buffer containing 320 mM of PAG and 160 mM of 7-ADCA methylsulfonylethyl ester and the mixture was allowed to react with stirring at 37°C for 16 hours. Then, 12 ml. of tetrahydrofuran was added and the cells and insoluble proteins were removed by centrifugation. Finally, the concentration of 7-phenylacetamido-3-desacetoxycephalosporanic acid methylsulfonylethyl ester in the resultant 75 % aqueous tetrahydrofuran solution was measured by polarimetry. The yield was 44 mM for the reaction mixture containing the cells of *Pseudomonas putida* IFO-3537 or 36 mM for the system containing the cells of *Proteus rettgeri* ATCC-9250.

EXAMPLE 7

Ten (10) ml. of a 20 % aqueous solution of methanol containing 160 mM of TAG and 80 mM of 7-ADCA methyl ester was pooled with 10 ml. of a suspension of the washed cells of *Escherichia coli* IFO-13502 prepared according to Example 1 in 0.5M citrate-phosphate buffer (pH 6.0) and the mixture was allowed to react under stirring at 30°C for 3 hours. Then, the concentration of 7-(2'-thienylacetamido)-3-desacetoxycephalosporanic acid methyl ester in the reaction system was 28 mM as determined with polarimetry. The reaction was terminated by the addition of 50 ml. of a mixture of dichloromethane-ethyl ether (1:3) and the reaction mixture was shaken well to extract the contemplated cephalosporin ester. Using 50 ml. of a similar solvent, the extraction procedure was repeated further twice and the extracts were pooled and dried over anhydrous sodium sulfate. Then, the solvent was distilled off at a temperature not exceeding 35°C. The resultant residue was crystallized from a small quantity of methanol-water to obtain 155 mg. of needles, melting point: 196°–198°C, $[\alpha]_D^{25}$ +147°(c=0.5, in methanol). NMR(CDCL$_3$) δ(ppm): 2.07(3H,s), 3.25(2H,q), 3.75(3H,s), 3.77(2H,s), 4.87(1H,d), 5.67(1H,q), 6.72(1H,d), 6.90(2H,d), 7.17(1H,t)(s:singlet; d:doublet; t:triplet; q:quartet). The product was identified with an authentic sample by IR and NMR spectrometry.

EXAMPLE 8

The washed cells of *Escherichia coli* IFO-13502 as prepared according to Example 1 were suspended in 10 ml. of 0.5M citrate-phosphate buffer to four times the concentration of the culture broth.

To this suspension was added 10 ml. of a 20 % aqueous solution of methanol containing PAG(80mM) and 7-ADCA methyl ester (67.4 mM) and the mixture was reacted at 30°C with constant stirring. After 4 hours, the reaction product (7-phenylacetamido-3-desacetoxycephalosporanic acid methyl ester) amounted to 26.5 mM(79 % of theoretical). The quantitative analysis of the product was performed by spectrophotometry as applied in combination with the use of β-lactamase.

The reaction was terminated after four hours incubation and the reaction system was shaken well with 40 ml. of tetrahydrofuran. Then, the cellular and other insoluble materials were removed by centrifugation and the supernatant was concentrated under reduced pressure at a temperature not exceeding 35°C. The resultant crystals were harvested by filtration and recrystallized from methanol. The procedure yielded needles of 7-phenylacetamido-3-desacetoxycephalosporanic acid methyl ester, melting point: 191°–193°C, $[\alpha]_D^{25}$ +23°(c=0.5, in CH$_2$Cl$_2$), $E_{1cm}(260$ m$\mu$)=185. The product was identified with an authentic sample by IR and NMR spectrometry.

EXAMPLE 9

The washed cells of *Escherichia coli* IFO-13502 as prepared according to Example 1 were suspended in 20 ml. of distilled water to a concentration ten times that of the culture broth. To this suspension was added 20 ml. of a 20 % aqueous solution of methanol containing 320 mM of TAG and 160 mM of 7-ACA methoxymethyl ester and the system was reacted at 28°C, the pH being controlled at 6.0 by means of a pH-stat. After 4 hours, the accumulation of the contemplated cephalosporin ester in the reaction mixture was 61 mM. The quantitative analysis was conducted by spectrophotometry as applied in combination with the use of β-lactamose. Then, 120 ml. of tetrahydrofuran was added to the reaction mixture to completely dissolve the product and the cells and other insolubles are removed by filtration. The resultant supernatant was concentrated under reduced pressure and at a temperature not exceeding 30°C and the resultant crystalline residue was harvested by filtration, washed with water and recrystallized from methylene chloride and ether. The procedure yielded 203 mg. of 7-(2'-thienylacetamido)cephalosporanic acid methoxymethyl ester, melting point: 158°–159°C$[\alpha]_D^{25}$ + 28°(c=0.5, in CH$_2$Cl$_2$), $E_{1cm}^{1\%}(260$m$\mu$)=162.

The product was identified with an authentic sample by NMR and IR spectrometry.

EXAMPLE 10

A loopful of *Escherichia coli* IFO-3450 from a 2-day slant culture was used to inoculate each 25 ml. of medium B in a shake flask of 200 ml. capacity and cultivated under shaking at 24°C for 24 hours.

Then, the culture fluids from the four flasks were centrifuged to obtain the grown cells, which were then suspended in 10 ml. of 0.2M citrate-phosphate buffer (pH 6.0). To this suspension was added 10 ml. of 0.2M citrate-phosphate buffer containing 160 mM of phenylacetamide and 80 mM of 7-ADCA methylsulfonylethyl ester. The system was reacted under stirring at 37°C for 16 hours. The yield of 7-phenylacetamido-3-desacetoxycephalosporanic acid methylsulfonylethyl ester in the reaction system was 24.2 mM.

EXAMPLE 11

The washed cells of *Escherichia coli* IFO-13502 as prepared according to Example 1 were suspended in 10 ml. of 0.5M citrate-phosphate buffer (pH 6.0) to a concentration ten times that of the culture broth. To the resultant suspension was added 10 ml. of a 20 % aqueous solution of methanol containing TAG (160 mM) and 7-ACA acetonyl ester (80 mM) and the mixture was reacted under stirring at 30°C. After 4 hours, the yield of cephalosporin ester as accumulated in the reaction mixture was 20.5 mM. Then, 40 ml. of tetrahydrofuran was added and, after shaking well, the cells and other insolubles were removed by centrifugation. The supernatant was concentrated at low temperature under reduced pressure. The resultant crystals were harvested by filtration and recrystallized from methanol-ether. The procedure yielded 128 mg of 7-(2'-thienylacetamido)cephalosporanic acid acetonyl ester. This product was identified with an authentic sample by NMR and IR spectrometry.

EXAMPLE 12

The washed cells of *Escherichia coli* IFO-13502 as prepared according to Example 1 were suspended in 10 ml. of 0.5M citrate-phosphate buffer (pH 6.0) to a concentration 10 times that of the original culture broth and, then, 10 ml. of 20 % aqueous methanol containing TAG(120 mM) and 7-ACA diphenylmethyl ester (60 mM) was added. Under stirring, the mixture was allowed to react at 30°C. After 4 hours' reaction, the amount of cephalosporin ester as accumulated in the reaction system was 18.5 mM. To this reaction mixture was added 40 ml. of tetrahydrofuran and, after shaking well, the cells and other insolubles were removed by centrifugation. The supernatant was concentrated at low temperature under reduced pressure. The resultant crystals were harvested by filtration and recrystallized from methanol to obtain 105 mg. of 7-(2'-thienylacetamido)cephalosporanic acid diphenylmethyl ester, melting point: 61°–63°C, $[\alpha]_D^{25}$ 0°(c=0.5, $CH_2Cl_2$), $E_{1cm}^{1\%}(260\ m\mu)$=136. This product was identified with an authentic sample by NMR and IR spectrometry.

EXAMPLE 13

There was prepared 20 ml. of an aqueous solution (adjusted to pH 6.0) containing 480 mM of TAG and 240 mM of 7-ADCA methylsulfonylethyl ester. Meanwhile, the washed cells of *Escherichia coli* IFO-13502 as prepared according to Example 1 were suspended in 20 ml. of distilled water to a concentration 10 times that of the original culture broth. The suspension was added to the above solution and the mixture was reacted at 37°C, the pH being maintained at 6.0 with 2N HCl by a pH-stat.

The yield of the cephalosporin ester accumulated in the reaction system by the end of 5 hours was 86.4 mM as measured by polarimetry.

The reaction was terminated at this time and 200 ml. of tetrahydrofuran was added to the mixture to dissolve the product. Then, the cells and other insolubles were removed by filtration. The resultant filtrate was concentrated under reduced pressure at a temperature not exceeding 35°C and the crystals separated were harvested by filtration. The crystals were then recrystallized from methanol-ether to obtain 1.26 g. of 7-(2'-thienylacetamido)-3-desacetoxycephalosporanic acid methylsulfonylethyl ester, melting point: 137°–139°C, $[\alpha]_D^{25}$+120°(c=0.5, in 75 % aqueous tetrahydrofuran), $E_{1cm}^{1\%}$ (260 m$\mu$=175, NMR(CDCl$_3$) δ (ppm): 2.13(3H,s), 2.94(3H,s), 3.33(2H,d), 3.38(2H,t), 3.83(2H,s), 4.65(2H,q), 4.95(1H,d), 5.73(1H,q), 6.67(1H,d), 6.98(2H,d), 7.25(1H,t).

EXAMPLE 14

In 7 l. of 0.1M Tris-hydrochloric acid buffer (pH 8) were suspended 2700 g. (on a wet basis) of washed cells of *Escherichia coli* IFO-13502 as prepared according to Example 1. Then, using a fractionator (Ribi Cell Fractionator, Sorval, Model RF-1), the cells were disrupted under 15000 p.s.i. To the resultant crude extract were added 17.3 g. of MgSO$_4$. 7H$_2$O(final concentration: 10mM) and 3.5 mg. of DNase-I(Sigma, final concentration 0.5 $\mu$g/ml.) and the system was stirred at 5°C for 3 hours. Then, 282 g. of Ca(CH$_3$COO)$_2$. H$_2$O was added in powdery form and dissolved. Thereafter, a solution of 279 g. of K$_2$HPO$_4$ in 800 ml. of pure water was gradually added dropwise to cause calcium phosphate gel to be formed in the crude extract and the system was promptly centrifuged. The resultant supernatant, amounting to 7.9l., was brought to pH 5.2 with 10 % acetic acid and, after the resultant precipitate was removed by centrifugation, was further adjusted to pH 7.5 with 2 % aqueous ammonia. Then, ammonium sulfate powder was added to the solution to 60 % saturation and the precipitate was harvested by centrifugation, dissolved in a small quantity of pure water and dialyzed against pure water. The resultant dialysate, 1.1 l., was passed over diethylaminoehtylcellulose (pH 8.5, 0.01M Tris-buffer) and the cephalosporin-synthesizing enzyme adsorbed was eluted with 0.01M Tris-HCl buffer (pH 8.5) containing 0.05M NaCl. The fractions having activity were pooled and dialyzed against pure water, followed by lyophilization, whereupon about 730 mg. of enzyme preparation was obtained.

An example of synthesis of cephalosporin ester by use of the above enzyme preparation is as follows.

Twenty(20) mg. of the above enzyme preparation was added to a 20 ml. aqueous solution (pH 6.0) containing 160 mM of TAG and 80 mM of 7-ADCA methylsulfonylethyl ester and the mixture was reacted at 37°C for 4 hours, the pH being held at 6.0 with 2N HCl by means of a pH-stat. It was found that, during this reaction time, 58.2 mM of 7-(2'-thienylacetamido)-3-desacetoxycephalosporanic acid methylsulfonylethyl ester had accumulated in the system. The quantitative determination was carried out by polarimetry.

EXAMPLE 15

The cephalosporin ester-synthesizing enzyme according to Example 14 was chemically bound to a water-insoluble resin to prepare a water-insoluble enzyme preparation and a cephalosporin ester synthesis was carried out with the aid of this enzyme preparation. A number of known methods are available for binding the cephalosporin ester-synthesizing enzyme to a water-insoluble resin. For the present purpose, however, the azide method only will be mentioned and described as an example of the available insolubilization procedure.

In 400 ml. of methanol was suspended 50 g. of carboxymethylcellulose (CMC) (Whatman CM-11) and while the suspension was cooled at −10°C to −20°C, 100 ml. of thionyl chloride was added dropwise. The reaction was further allowed to proceed overnight under cooling with ice and, then, for 3 days at room temperature. The methyl ester thus formed was harvested by filtration, washed with methanol, acetone and ether, and finally dried (yield 41 g.). Then, this methyl ester was suspended in 500 ml. of methanol and 100 ml. of hydrazin hydrate was added. The mixture was refluxed at 65°C for 3 hours and, then, allowed to stand at room temperature overnight. The resultant CMC-hydrazide was washed with methanol and ether and dried (yield 39.3 g.). Three (3) g. of the CMC-hydrazide was added to a mixture of 150 ml. of 2 % hydrochloric acid and 30 ml. of 3 % sodium nitrite and the mixture was allowed to react at 4°C for 30 minutes. The product was harvested by filtration and washed twice with 200 ml. of cold dioxane and, then, with 200 ml. of cold water to obtain CMC-azide. Then, 1 g. of the CMC-azide was suspended in 5 ml. of 0.05M phosphate buffer (pH 8.0) and a solution of 100 mg. of the cephalosporin ester-synthesizing enzyme according to Example 14 in 10 ml. of a similar buffer was added. The mixture was reacted overnight at 5°C. The resultant product was harvested by filtration and washed well with 0.2M aqueous glycine and, then, with 0.5M aqueous of sodium chloride. Then, the product was assayed for cephalosporin ester-synthesizing activity. It was found that 12 % of the activity of the enzyme sample used had been bound to the CMC. The entire amount of the water-insoluble enzyme thus obtained was suspended in 20 ml. of 0.2M citrate-phosphate buffer (pH 6.0) and a solution of 160 mM of TAG and 80 mM of 7-ADCA methylsulfonylethyl ester in 20 ml. of a similar buffer was added. The mixture was allowed to react at 37° C for 4 hours, with constant stirring, whereupon 28.2 mM of 7-(2'-thienylacetamido)-3-desacetoxycephalosporanic acid methylsulfonylethyl ester accumulated in the reaction mixture. The quantitative determination was conducted by polarimetry.

EXAMPLE 16

The washed cells of *Escherichia coli* IFO-13502 as prepared according to Example 1 were suspended in 10 ml. of 0.5M citrate-phosphate buffer to a concentration 10 times that of the original culture broth and, then, 10 ml. of a similar buffer containing 160 mM of TAG and 80 mM of 7-amino-3-(2''-pyridylthiomethyl)3-cephem-4-carboxylic acid methoxymethyl ester was added. The mixture was allowed to react at 37°C for 4 hours, with constant stirring, whereby 24 mM of 7-(2'-thienylacetamido)-3-(2''-pyridylthiomethyl)-3-cephem-4-carboxylic acid methoxymethyl ester was produced in the reaction mixture. The quantitative determination was conducted by polarimetry.

EXAMPLE 17

The washed cells of *Escherichia coli* IFO-13502 as prepared according to Example 1 were suspended in 10 ml. of 0.5M citrate-phosphate buffer to a concentration ten times that of the original culture broth and, then, 10 ml. of a similar buffer containing 160 mM of TAG and 80 mM of 7-amino-3-{6''-(3''-methylpyridazinyl)thiomethyl}-4-methoxymethoxycarbonyl-3-cephem-2''-oxide was added. Under stirring, the mixture was reacted at 37°C for 4 hours, whereby 22 mM of 7-(2'-thienylacetamido)-3-{6''-(3'''-methylpyridazinyl)thiomethyl}-4-methoxymethoxycarbonyl-3-cephem-2''-oxide was produced and accumulated in the reaction system. The quantitative determination was conducted by polarimetry.

EXAMPLE 18

The washed cells of *Escherichia coli* IFO-13502 as prepared according to Example 1 were suspended in 10 ml. of 0.5M citrate-phosphate buffer to a concentration ten times that of the original culture broth and, then, 10 ml. of a similar buffer containing 160 mM of TAG and 80 mM of 7-amino-3-{6''-(3'''-methoxypyridazinyl)thiomethyl}-4-methoxymethoxycarbonyl-3-cephem-1''-oxide was added. The mixture was allowed to react under stirring at 37° for 4 hours, whereupon 27 mM of 7-(2'-thienylacetamido)-3-{6''-(3'''-methoxypyridazinyl)thiomethyl}-4-methoxymethoxycarbonyl-3-cephem-1''-oxide was produced and accumulated in the reaction mixture. The quantitative determination was conducted by polarimetry.

EXAMPLE 19

The washed cells of *Escherichia coli* IFO-13502 as prepared according to Example 1 were suspended in 10 ml. of 0.5M citrate-phosphate buffer to ten times the concentration of the original culture broth. Then, 10 ml. of a similar buffer solution containing 160 mM of TAG and 80 mM of N-{7-amino-4-methoxymethoxycarbonyl-3-cephem-3-ylmethyl}pyridinium is added to the suspension. The mixture is allowed to react under stirring at 37° for 4 hours, whereupon 21 mM of N-{7-(2'-thienylacetamido)-4-methoxymethoxycarbonyl-3-cephem-3-ylmethyl}pyridinium was produced and accumulated in the reaction mixture. The quantitative determination was conducted by polarimetry.

EXAMPLE 20

The washed cells of *Escherichia coli* IFO-13502 as prepared according to the manner in Example 1 were suspended in 2 ml. of 0.2M phosphate buffer to a concentration 20 times that of the original culture broth and, then, 2 ml. of a 0.2M phosphate buffer containing 160 mM of 7-ADCA methylsulfonylethyl ester and 320 mM of 0-(p-hydroxyphenylacetyl)-glycolic acid was added. The mixture was allowed to react at 37°C for 16 hours with constant stirring. The cephalosporin ester thus formed and unreacted 7-ADCA ester were converted to the corresponding acids with 180 mM of NaOH at 25°C, pH 10.0. The mixture was treated with β-lactamase produced by Aerobacter cloaceae IFO-12937 according to the manner of Reference Example 1 and a concentration of the cephalosporin was measured by spectrophotometry. The amount of 7(p-hydroxyphenylacetamido)-3-desacetoxycepharosporanic acid methylsulfonylethyl ester accumulated in the reaction system was 118 mM.

EXAMPLE 21

A similar manner to that of Example 20 was conducted using the washed cells of *Proteus rettgeri* ATCC-9250 instead of *Escherichia coli* IFO-13502. The amount of 7-(p-hydroxyphenylacetamido)-3-desacetoxycephalosporanic acid methylsulfonylethyl ester accumulated in the reaction system was 9 mM.

EXAMPLE 22

To 20 ml. of the culture of *Bacillus sp.* ATCC-14552 prepared by the same manner as that of Example 5 was added 164 mg. of phenylacetic acid ethyl ester dissolved in 2.5 ml. of methanol and 178 mg. of 7-amino-3desacetoxycephalosporanic acid methylsulfonylethyl ester hydrochloride dissolved in 2.5 ml. of 0.5M phosphate buffer (pH 8.0). The mixture was adjusted to pH 8.5 with 5-NaOH and allowed to react at 37°C for 24 hours with constant stirring. The amount of 7-phenylacetamido-3-desacetoxycephalosporanic acid methylsulfonylethyl ester as accumulated in the reaction system was 12.3 mM. The determination was made by spectrophotometry as applied in combination with the use of β-lactamase.

EXAMPLE 23

The washed cells of *Escherichia coli* IFO-13502 prepared according to the manner in Example 1 were suspended in 0.5M phosphate buffer to a concentration 20 times that of the original culture broth. To 5 ml. of the suspension were added 5 ml. of 0.5M phosphate buffer (pH 8.0) containing 160 mM of phenylacetamide and 80 mM of 7-amino-3-desacetoxycephalosporanic acid methylsulfonylethyl ester and the mixture was allowed to react at 37°C for 24 hours. The amount of 7-phenylacetamido-3-desacetoxycephalosporanic acid methylsulfonylethyl ester as accumulated in the reaction system was 22.5 mM. The determination was made by polarimetry.

EXAMPLE 24

The cells of *Proteus rettgeri* ATCC-9250 were separated from 40 ml. of the culture prepared by a manner similar to that of Example 6 by centrifugation and were suspended in 2 ml. of 0.2M citrate-buffer (pH 6.0). To the suspension was added 2 ml. of a similar buffer containing 320 mM of S-phenylacetylthioglycolic acid and 160 mM of 7-amino-3-desacetoxycephalosporanic acid methylsulfonylethyl ester. The mixture was allowed to react at 37°C for 24 hours with stirring. The amount of 7-phenylacetamido-3-desacetoxycephalosporanic acid methylsulfonylethyl ester as accumulated in the reaction mixture was 57 mM. The determination was made by polarimetry.

EXAMPLE 25

To 20 ml. of the culture of *Bacillus sp.* IFO-12063 prepared by the same manner as that of Example 5 was added 5 ml. of 0.2M glycine-NaOH buffer (pH 9.0) containing 400 mM of phenylacetylglycine and 200 mM of 7-amino-3-desacetoxycephalosporanic acid methyl ester. The mixture was adjusted to pH 9.3 and allowed to react at 37°C for 24 hours with stirring. The amount of 7-phenylacetamido-3-desacetoxycephalosporanic acid methyl ester as accumulated in the reaction system was 16 mM. The determination was made by polarimetry.

What is claimed is:

1. A method for the production of a cephalosporin of the formula:

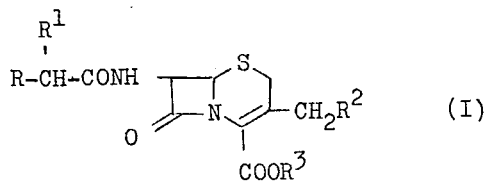

wherein R is an unsaturated six-membered carbocyclic ring or five-membered heterocyclic ring residue which may have uncharged substituent(s); $R^1$ hydrogen, hydroxy, or halogen; $R^2$ is a hydrogen atom or an organic group which is bound through an oxygen, sulfur or nitrogen atom; $COOR^3$ is an ester group which may be easily converted to COOH, which comprises reacting a derivative of an organic acid of the formula:

wherein R and $R^1$ have the same meaning as defined above with 7-aminocephem-4-carboxilic acid ester of the formula:

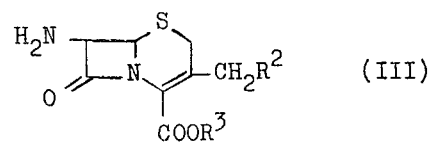

wherein $R^2$ and $COOR^3$ have the same meaning as defined above in the presence of a culture or the enzyme containing processed matter of said culture of the microorganism of one of the genera *Escherichia*, *Bacillus*, *Proteus* and *Pseudomonas* which is able to synthesize a cephalosporin of the formula (I) from a derivative of the organic acid of the formula (II) and 7-aminocephem-4-carboxylic acid ester of the formula (III).

2. A method according to claim 1, wherein the derivative of the organic acid of the formula (II) is one which can be hydrolyzed in aqueous medium in the presence of a culture or a processed matter of the microorganism employed to give the organic acid of the formula (II).

3. A method according to claim 1, wherein $R^2$ is hydrogen, alkoxy, alkylcarbonyloxy, pyridylthio, pyridinium, alkylthiocarbonyloxy, dialkylaminothiocarbonylthio, alkylammonium, $-N_3$, aralkyloxycarbonylamino or pyridazinylthio-N-oxide and $R^3$ is halogenoalkyl, alkyl(or aryl) sulfonylalkyl, alkyl, alkoxyalkyl, alkylcarbonylakyl, diarylthioalkyl or alkyl (or aryl) sulfinylalkyl.

4. A method according to claim 2, wherein $R^2$ is hydrogen, alkoxy, alkylcarbonyloxy, pyridylthio, pyridinium, alkylthiocarbonyloxy, dialkylaminothiocarbonylthio, alkylammonium, $-N_3$, aralkyloxycarbonylamino or pyridazinylthio-N-oxide and $R^3$ is halogenoalkyl, alkyl (or aryl) sulfonylalkyl, alkyl, alkoxyalkyl, alkylcarbonylalkyl, diarylthioalkyl or alkyl (or aryl) sulfinylalkyl.

5. A method according to claim 4, wherein the derivative of the organic acid of the formula (II) is an amino acid ester, a glycolic acid ester, a thioglycolic acid ester, an amide or alkyl ester of the said organic acid.

6. A method according to claim 1, wherein the microorganism is *Escherichia coli*.

7. A method according to claim 4, wherein the microorganism is
*Escherichia coli* IFO-3542,
*Escherichia coli* ATCC-9637,
*Escherichia coli* var. *communior* IFO-3547,
*Escherichia coli* var. *communior* IFO-3548,
*Escherichia coli* IFO-13502,
*Escherichia coli* IFO-3470,
*Escherichia coli* IFO-3450,
*Bacillus sp.* IFO-12063,
*Proteus rettgeri* ATCC-9250 or
*Pseudomonas putida* IFO-3537.

* * * * *